(12) United States Patent
Martinez Sanz et al.

(10) Patent No.: US 10,379,034 B2
(45) Date of Patent: Aug. 13, 2019

(54) SPECTROPHOTOMETER FOR THE CHARACTERISATION OF RECEIVERS OF SOLAR COLLECTORS

(71) Applicant: ABENGOA SOLAR NEW TECHNOLOGIES, S.A., Seville (ES)

(72) Inventors: Noelia Martinez Sanz, Seville (ES); Guillermo Espinosa Rueda, Seville (ES); David Izquierdo Núñez, Seville (ES); Marta Osta Lombardo, Seville (ES); Marta Mainar López, Seville (ES); Carlos Heras Vila, Seville (ES); Iñigo Salina Ariz, Seville (ES); Santiago Forcada Pardo, Seville (ES); Rafael Alonso Esteban, Seville (ES)

(73) Assignee: ABENGOA SOLAR NEW TECHNOLOGIES, S.A., Seville (ES)

( * ) Notice: Subject to any disclaimer, the term of this patent is extended or adjusted under 35 U.S.C. 154(b) by 627 days.

(21) Appl. No.: 15/021,543

(22) PCT Filed: Sep. 12, 2014

(86) PCT No.: PCT/ES2014/000145
§ 371 (c)(1),
(2) Date: Mar. 11, 2016

(87) PCT Pub. No.: WO2015/036631
PCT Pub. Date: Mar. 19, 2015

(65) Prior Publication Data
US 2016/0238519 A1    Aug. 18, 2016

(30) Foreign Application Priority Data
Sep. 13, 2013   (ES) .................................. 201300845

(51) Int. Cl.
*G01N 21/27*     (2006.01)
*G01N 21/25*     (2006.01)
(Continued)

(52) U.S. Cl.
CPC ............ *G01N 21/27* (2013.01); *G01J 3/0202* (2013.01); *G01J 3/0254* (2013.01); *G01J 3/0264* (2013.01);
(Continued)

(58) Field of Classification Search
CPC ...... G01N 21/27; G01N 21/255; G01N 21/55; G01N 21/59; G01N 2201/0221;
(Continued)

(56) References Cited

U.S. PATENT DOCUMENTS 4,859,861 A * 8/1989 Mersch .................. G01B 11/08
                                                          250/559.22
9,435,747 B2 * 9/2016 Song ...................... G01N 21/87
(Continued)

FOREIGN PATENT DOCUMENTS

JP    H06347326 A    12/1994
JP    2000266517 A    9/2000
(Continued)

OTHER PUBLICATIONS

International Search Report for corresponding International Application No. PCT/ES2014/000145.

*Primary Examiner* — Georgia Y Epps
*Assistant Examiner* — Don J Williams
(74) *Attorney, Agent, or Firm* — Egbert Law Offices, PLLC

(57) ABSTRACT

Spectrophotometer for the characterization of receivers of solar collectors in order to determine optical properties (transmittance and reflectance). The equipment allows the evaluation of a receiver tube in real time and in any kind of (Continued)

light conditions, both inside and outside. The equipment also allows the detection of the eccentricity between the outer tube and the inner tube, which directly influences the reliability of the measurement. The equipment has a mechanical system for allowing a rotation of the equipment around the tube in order to find the optimum measurement position and attach itself to the tube.

15 Claims, 4 Drawing Sheets

(51) Int. Cl.
| | |
|---|---|
| *G01J 3/02* | (2006.01) |
| *G01J 3/10* | (2006.01) |
| *G01N 21/55* | (2014.01) |
| *G01N 21/59* | (2006.01) |
| *G01J 3/42* | (2006.01) |
| *F24S 20/20* | (2018.01) |
| *F24S 10/40* | (2018.01) |

(52) U.S. Cl.
CPC ................. *G01J 3/10* (2013.01); *G01J 3/108* (2013.01); *G01J 3/42* (2013.01); *G01N 21/255* (2013.01); *G01N 21/55* (2013.01); *G01N 21/59* (2013.01); *F24S 10/45* (2018.05); *F24S 20/20* (2018.05); *G01J 2003/102* (2013.01); *G01N 2201/0221* (2013.01); *G01N 2201/062* (2013.01); *G01N 2201/065* (2013.01); *G01N 2201/0625* (2013.01); *G01N 2201/0627* (2013.01); *G01N 2201/12* (2013.01)

(58) Field of Classification Search
CPC ..... G01N 2201/062; G01N 2201/0625; G01N 2201/0627; G01N 2201/065; G01N 2201/12; G01J 3/0202; G01J 3/0254; G01J 3/0264; G01J 3/10; G01J 3/42
See application file for complete search history.

(56) References Cited

U.S. PATENT DOCUMENTS

| | | |
|---|---|---|
| 2004/0099058 A1 | 5/2004 | Edvardsson |
| 2007/0184373 A1* | 8/2007 | Mertens ................... G01J 3/46 430/65 |
| 2010/0243902 A1* | 9/2010 | Wada ....................... G01J 3/02 250/339.08 |

FOREIGN PATENT DOCUMENTS

| | | |
|---|---|---|
| KR | 20080114331 A | 12/2008 |
| WO | 2011104401 A1 | 9/2011 |

* cited by examiner

SPECTROPHOTOMETER FOR THE CHARACTERISATION OF RECEIVERS OF SOLAR COLLECTORS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention falls within the technological field of optical measuring instruments or equipment.

More particularly it relates to portable equipment for spectral and field characterisation of the reflection or reflectance coefficients and the transmission or transmittance coefficient of the receiver tubes used in thermal solar parabolic trough technology. The equipment includes all the components necessary to perform such measurement, mechanical adjustment to the tube, emission and detection of signals, processing of signals, display of results on screen and memory storage unit.

2. Description of Related Art Including Information Disclosed Under 37 CFR 1.97 and 37 CFR 1.98

Solar energy collection, in its aspect of thermal collection, is becoming ever more technologically and economically important for the domestic production of hot water, heating or cooling and for the production of electricity in solar thermal power plants.

These systems require a maximum absorption of solar energy and the least possible energy losses. To this end, in parabolic collectors, receivers are configured by two concentric tubes: a first outer glass tube inside which there is an inner absorber metal tube usually made of steel, existing between them vacuum conditions that reduce losses due to conduction and convection. The inner tube has a coating with great solar energy absorbing power and low emissivity characteristics to reduce energy losses by thermal radiation in the far infrared spectrum.

Consequently, both in the domestic context and in the production of electricity, selective absorber coatings play an essential role and their proper functioning largely conditions the performance of such systems. This makes it vitally important to have a suitable device and a field characterisation method of the optical properties of these coatings. In the case of electricity production installations, due to the large number of absorber tubes to be characterised, it is also desirable that measurements can be taken quickly and easily.

Given the optical characteristics of such tubes (maximum energy absorption and minimum energy loss), the equipment must be capable of accurately measuring extreme values of the coefficients of reflection and transmission (close to zero or to a unit), generally in unfavourable environmental conditions because, logically, the ambient light is almost always of a high intensity.

Since these reflection and transmission coefficients depend on the wavelength of light in which they are evaluated, it is essential to perform a spectral characterisation thereof. Equipment taking this type measurement is called a spectrophotometer.

A classic spectrophotometer uses a light source with a broad spectrum and a variable filtering element, such as a mobile diffraction network followed by a narrow slit, making it possible to sequentially select different wavelengths. This option allows varying the wavelength almost continuously, however it is a more complex and delicate system and with a low dynamic range of measurement, since the input light power achieved is very low.

U.S. Pat. No. 4,687,329 describes equipment that uses a wide spectrum source, in this case ultraviolet spectrum, and various filters in fixed positions for spectral measurement at a number of discrete points.

Other prior registrations relate to spectrophotometers which use a collection of sources of different wavelengths as the light source. In US2008/0144004 several light emitting diodes (LED) are simultaneously used to perform a transmission measurement for the detection of various analytes in blood. However, it is not a true spectral measurement, yet several simultaneous measurements at a few different wavelengths. In addition, there is no protection against ambient light and reflection and reference measurements are not possible.

Something similar happens in the invention disclosed in U.S. Pat. No. 4,286,327, wherein a sequential measurement at different wavelengths (in the infrared spectrum) is indeed performed, but in this case the LEDs used are identical and the spectral selection is conducted by means of fixed filters with a different central wavelength. Neither is there a mechanism for recovering the signal away from ambient light, nor the possibility of performing reflection or reference measurements.

None of the above equipment or other similar ones meet the requirements for the field measurement of absorbent tubes for solar collectors, either based on range, sensitivity and/or mechanical configuration.

WO 2011/104401 is especially noteworthy. The main differences between WO 2011/104401 and the invention are pointed out below.

1) The device claimed in WO 2011/104401 requires a different optical channel for each wavelength in which it is measured, both in reflection and in transmission, while the equipment of the invention requires a single optical channel and running within, a radiation comprising the wavelengths of interest for measurement.

2) WO 2011/104401 fails to include any alignment system to detect the non-concentricity of the inner and outer tube of the receiver.

3) WO 2011/104401 fails to present an integrated visual interface in the device itself and communicates with a computer via a wireless network.

4) WO 2011/104401 has no mechanical adjustment of the equipment to the receiver tube.

5) WO 2011/104401 has no data storage unit.

6) The equipment described in WO 2011/104401 performs spectral measurements based on a set of LEDs arranged in line located on the equipment along the receiver tube, so there is an optical channel for each LED implemented. Each optical measurement channel is formed by a LED, a reference detector and a measurement detector, making a high number of detectors used in the equipment, which increases the complexity of the equipment. This optical configuration of the equipment determines the size of the equipment depending on the number of LEDs, the greater the number of LEDs, the larger the size of the equipment.

7) Both the system of WO 2011/104401 and that of the invention are affected by temperature variations, since the intensity of the radiation emitted by a LED, and shape of the beam, may vary with temperature. However, this unwanted interference of temperature in the operation of the WO 2011/104401 system, cannot be compensated or corrected because the detection and reference system is not configured to detect measurement alterations caused by temperature.

This is because in the system of WO 2011/104401 the reference detector does not receive all the light emitted by the LED, since the reference detector is located next to the LED and does not detect the entire surface of the LED (it has a biased view of it) and therefore neither does it detect the full beam of radiation emitted by it.

For this reason, the device of WO 2011/104401 does not ensure measuring the same light radiated in reference as in measurement, while the reflectivity and transmissivity measurement is less reliable than that of the device of the invention, due to possible variations in the beam due to temperature not detected by the reference detector.

8) In addition the system of WO 2011/104401 has no uniformity of the measurement beams because it directly uses the radiation from the LEDs. For this reason, the system has no sensitivity to changes in position of the tubes, i.e. the system has what is referred to in the description as a lack of geometric tolerance.

9) The present invention can comprise integrating spheres, which, in addition to optimising the space and the number of components used, allows to homogenise the light beam emitted, thereby improving signal quality.

The invention solves the problems described above by lightweight portable equipment that is fully autonomous, mechanically adjustable to the tube, which enables rapid execution and processing of measurements, and with suitable sensitivity and accuracy.

BRIEF SUMMARY OF THE INVENTION

The invention relates to a portable spectrophotometer for the determination of optical properties (transmittance and reflectance) of a receiver tube of parabolic trough collectors (PTC). The equipment allows the optical evaluation of a receiver tube in real time and in any kind of light conditions, both inside and outside. The spectrophotometer may have two optical channels, one for measuring the transmittance and another for measuring reflectance. Each optical channel may comprise a plurality of LEDs of different wavelengths and photodetectors. These elements can be housed in integrating spheres that allow homogenisation of the light beam emitted improving the signal. The integrating spheres also optimise the dimensions of the equipment and minimise optical components, achieving a lightweight and compact set. The signal processing can be done using a lock-in algorithm to increase the signal-to-noise ratio and eliminate the influence of external light sources such as natural light. The equipment also evaluates the existence of eccentricity between the outer tube and the inner tube, which directly influences the reliability of the measurement. The equipment may have a mechanical system to allow rotation of the equipment around the tube in order to find the optimum measurement position and to attach itself to the tube. The interaction with the equipment can be done using a screen-keyboard interface that enables communication with the equipment and the display of real-time measurements. Data can be stored in an external memory unit, which can be integrated into the equipment itself.

To achieve a simple and robust system, the lighting of the tubes, both the outer tube (usually borosilicate glass) and the inner absorber pipe (usually steel) can be done by light emitting diodes (LED) which cover the range of wavelengths in which the characterisation is desired. This allows for a cheap source of stable and lasting light. The existence of commercial LEDs in a large number of wavelengths in the range 300 to 2500 nm allows performing the spectral measurement in the desired resolution, selecting the appropriate number of LEDs depending on the specific characteristics of each problem. For spectral characterisation of a component in the solar thermal industry, it may be sufficient to have around fifteen measurement wavelengths.

In order to improve the emission signal of these LEDs, integrating lighting spheres that house a given number of LEDs may be used. Thus, to generate the incident measuring light beam, the LED array can be placed illuminating inside an integrating sphere whose inner walls have a high reflectivity factor in the emission wavelengths of the LEDs implemented. On the inner side of the sphere a detector can be placed to register a light level inside the sphere. Thus a measurement of the reference signal can be obtained that can be used to correct variations of light emission power of the LEDs due to temperature. This detector can operate in the spectral range of the LEDs placed in the sphere. An outlet hole in the integrating sphere can allow part of the light generated by the LEDs out of the sphere forming the incident light beam used in the measurement. Part of this light beam that comes out of the sphere can be collected by a lens either to collimate the beam, to form an image or to work with a divergent beam, depending on the distance at which the lens and its focus are placed. A part of this beam can be detected in the measurement detector, after passing through the glass tube in order to measure the transmittance or after being reflected on the inner absorber tube in order to measure reflectance.

The output incident beam from the integrating lighting sphere is a beam having a uniform field, which can provide the equipment with some amount of geometric tolerance in transmittance and reflectance measurements. This geometric tolerance implies that the equipment can detect and take into account geometric differences such as displacement of the inner tube relative to the coaxial axis or slight variations in diameter or thickness of the borosilicate tube. Moreover, to implement a reference signal measurement system based on the light level inside the sphere, power variations of LED light emission power with temperature can be corrected as the reference detector, being placed inside the integrating sphere, can detect the entire beam emitted by the LEDs, that is, it no longer has a biased view of it.

Therefore, by including in the device of the invention the LEDs in integrating spheres, which generate optical signals used for spectral transmission measurement of the glass tube and spectral reflection measurement of the inner tube in solar collector tubes, the following advantages are achieved: a set of LEDs share a single reference detector and a single measurement detector, thereby reducing the equipment size and the number of detectors involved, it allows to obtain illuminating light beams with high uniformity which gives the equipment tolerance in terms of the position of the tubes and deflection of rays, and it eliminates the problem of variations in the LED emission reference pattern due to temperature by incorporating the reference detector in the measurement of the existing light inside the sphere, which eliminates measurement errors caused by the equipment temperature. The equipment may comprise two integrating spheres, a first sphere for the optical channel of transmittance and a second sphere for the optical channel of reflectance, or two integrating spheres for each optical channel. To obtain a sufficiently rapid measurement, the equipment can perform simultaneously without any adjustment between the first sphere(s) and the second sphere(s), the transmittance and reflectance measurement in each of the implemented wavelengths, as well as a reference measurement in each sphere.

The invention may also comprise an optical detection system of alignment or concentricity, to ensure that a position of the measuring equipment on the surface of the glass tube is correct relative to the position of the inner tube of the equipment.

The invention may also comprise positioning means consisting of a clamp that allows placing the equipment on or removing it from the tube, with a mechanism allowing to open the clamp to place the equipment on or remove it from the tube, or to close it around the receiver tube whereby the equipment is fixed to it in any position and without needing to hold it, and a plurality of rollers that allow the rotation of the equipment on a section of the receiver tube, whereby the equipment can comfortably rotate around the circumference of the glass tube to find the correct measurement position.

The rollers may be replaceable to adapt the equipment to different receiver tubes.

Thus, a lightweight equipment which is adaptable to the tube is achieved.

BRIEF DESCRIPTION OF THE DRAWINGS

For a better understanding of the invention, drawings are attached which, by way of example, show a practical case of the invention.

FIG. 3A is an equatorial view of the sphere and FIG. 3B is a polar view of the sphere.

DETAILED DESCRIPTION OF THE INVENTION

Figure 1A:
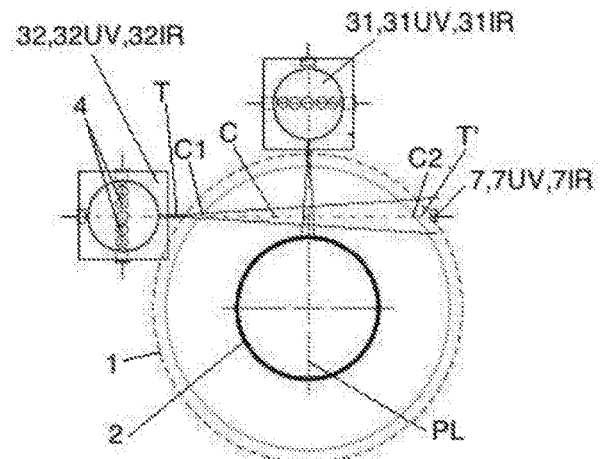
FIG. 1A Cross sectional diagram of the transmittance and reflectance measurement.

The general description of a preferred embodiment of the measuring device may be as follows:

A plurality of light emitting diodes or LEDs (4), covering the range of wavelengths in which the receiver tubes are to be characterised; in a preferred embodiment a pair of LEDs (4) for each wavelength could be used, one for measuring transmittance and another for measuring reflectance.

At least two integrating spheres (3), one for transmission and one for reflection, wherein said LEDs can be housed to optimise the uniformity of the light beam emitted and its scope, and to minimise the number of components used and minimise the size and complexity of the equipment.

Two photodetectors for each integrating sphere (3) used, in order to obtain the reflectance or transmittance and reference signals for all LEDs (4) housed in that sphere (3).

An alignment detection system that allows to assess at any time if there is relative displacement between the outer borosilicate tube (1) and the inner absorber tube (2), so that the required distances between the elements of the optical system are ensured. This alignment detection system may comprise a LED emitter (8) and an array of photodetectors (9) facing each other at one end and another with the diameter of the outer borosilicate tube (1). The LED (8) can be aligned with the midpoint of the array (9) of photodetectors. In turn, the system may be positioned so that the imaginary line connecting the LED with the array (9) centre is tangent to the inner tube (2).

A digital circuit that performs the analogue/digital acquisition and conversion of the signals of interest.

A digital processing card to extract the signal from the possible optical and electrical ambient background noise. This card can also undertake, if necessary, to apply the modulation chosen to the LED sources.

An interface consisting of a screen and keyboard which makes it possible to fully communicate with the equipment and display the equipment information and values measured in real time.

A GPS geo-location system that records the location of the measurements.

An external memory to store all equipment information and the values measured.

A central control and processing unit, which controls the overall operation of the system, selecting the electronic components corresponding to the channel used at each time and governing all the communications.

A casing that provides adequate insulation of the electronic and optical components of the system, permitting easy portability.

A mechanical system that allows the equipment to slide on the tube and attach the equipment onto the tube in any position.

An embodiment of the equipment may comprise an optical section or module for measurement, other electronics and other mechanics.

The optical section is key, as it must allow performing a simultaneous measurement of transmittance and reflectance of the tubes, with the required accuracy.

Figure 1B:
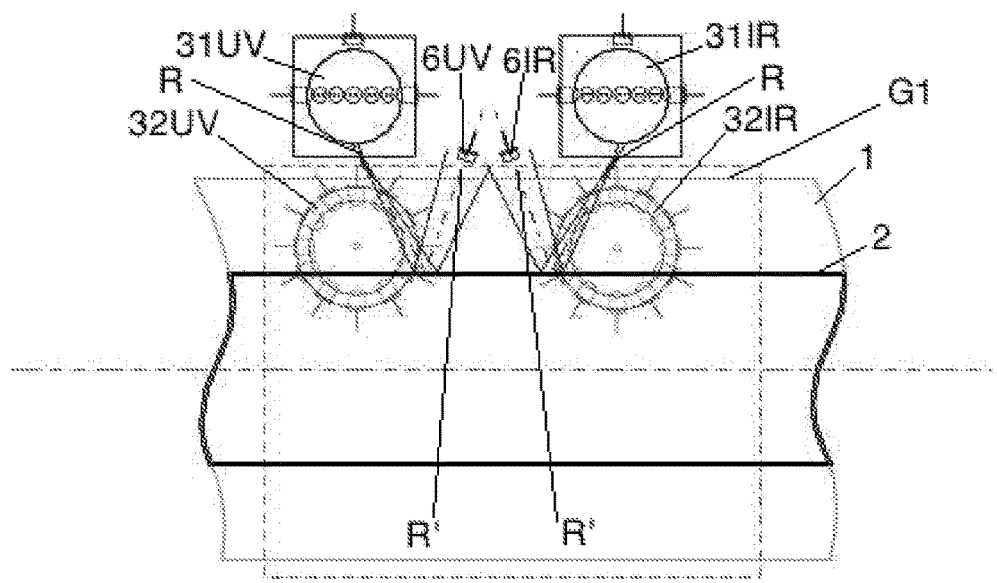
FIG. 1B Longitudinal diagram of the transmittance and reflectance measurement
Figure 2:
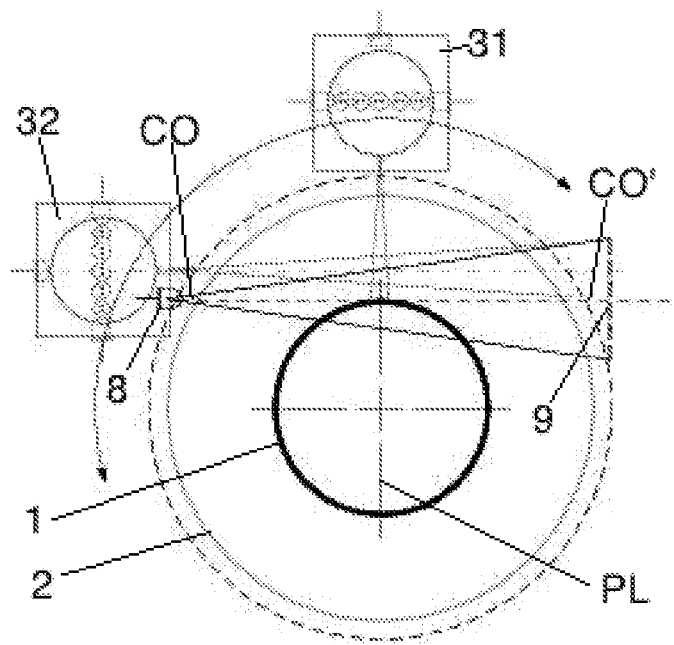
FIG. 2 Diagram of the alignment system measurement.

To achieve this, a preferred embodiment is proposed according to the arrangement of FIG. 1, and preferably including the following:

a first sphere (32IR) for the optical transmittance channel comprising LEDs (4) having wavelengths in the infrared spectrum;

a second sphere (32UV) for the optical transmittance channel comprising LEDs (4) having wavelengths in the ultraviolet and visible spectrum;

a third sphere (31IR) for the optical reflectance channel comprising LEDs (4) having wavelengths in the infrared spectrum;

a fourth sphere (31UV) for the optical reflectance channel comprising LEDs (4) having wavelengths in the ultraviolet and visible spectrum.

FIG. 1 shows how the transmittance and reflectance systems are arranged so that the light beams are perpendicular to each other. Each of these two systems is formed by two optical channels, one for the spectral measurement in the ultraviolet and visible range and another for the spectral measurement in the infrared range.

Each optical measurement channel can be formed by a set of LEDs, an integrating lighting sphere (3), a reference detector to determine the amount of light of the incident beam, a lens and a measurement detector for determining the light either transmitted, or reflected, as appropriate. Both detectors work in the spectral range covered by the LEDs implemented in the sphere.

In a preferred embodiment of the invention 14 LEDs have been chosen, 9 for the ultraviolet-visible (UV-VIS) spheres having wavelengths of 365, 405, 470, 525, 588, 655, 780, 870, 940 nm, and 6 LEDs for the infrared (IR) spheres having wavelengths of 940, 1050, 1300, 1550, 1720 and 1950 nm, covering the area of interest of the spectrum.

To generate the incident light beam in the measurement, each set of LEDs is placed illuminating the inside of an integrating sphere (3) together with the reference detector. This detector is preferably silicon for UV-VIS spheres and InGaAs for IR spheres. An outlet hole in the integrating sphere (3) allows part of the light generated by the LEDs out of the sphere forming the incident light beam used in the measurement. In the preferred embodiment, the LEDs and the reference detector are placed at the bottom of the sphere, around the outlet, thereby ensuring that there are no direct rays incident on the reference detector.

Figure 3A:
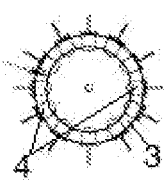
FIGS. 3A and 3B Position of LEDs within the integrating sphere.
Figure 3B:
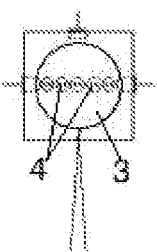
Figure 4:
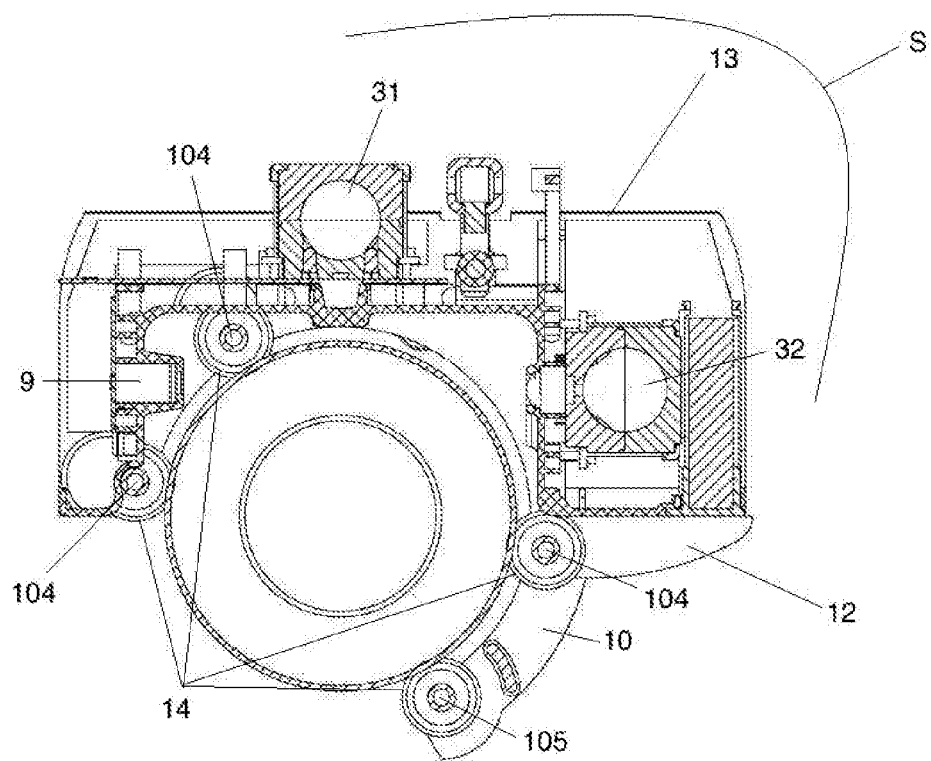
FIG. 4 Cross sectional view of the spectrophotometer
Figure 5:
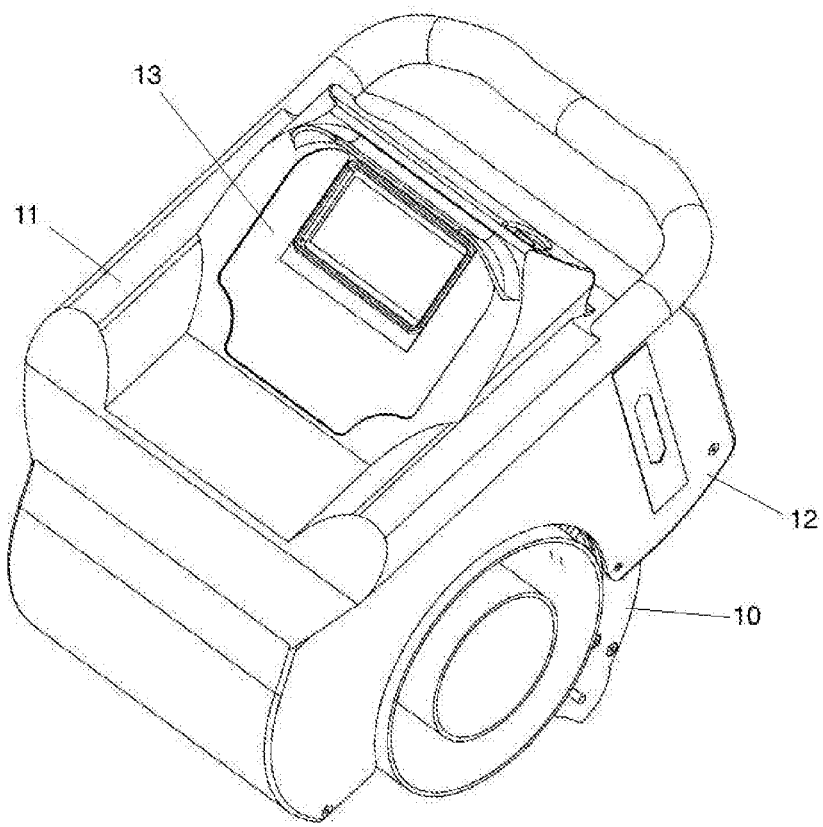
FIG. 5 Exterior view of the spectrophotometer

Part of the light beam coming out of the sphere is collected by a lens. In the case of optical transmission channels, the light beam exiting from the sphere is parallel to the normal to the surface of the sphere in which are LEDs are situated, the optical axis of the system is transverse to the tube and the beam light is incident on the tube at a height which ensures that the beam is not blocked by the inner steel tube, that is, it passes through the glass tube twice as shown in FIG. 3. While in the case of the optical reflection channels, the output beam of the integrating sphere (3) forms an angle of 12° with the normal to the surface of the sphere where the LEDs are located. This inclination allows positioning the measurement detector next to the emission source.

The receivers or tubes for parabolic trough collectors (PTC) are usually composed of two concentric tubes. The inner tube (2) must have a very low reflectance coefficient in the solar spectrum (high absorptance) and a high one in the thermal infrared spectral area (low emissivity), so that heat absorption is as high as possible. Moreover, the outer tube (1) should let through as much light as possible, equivalent to a transmittance coefficient close to the unit.

In order to obtain the transmittance measurement, the corresponding optical system emits light beams that pass through the outer borosilicate tube (1) twice, one input and one output. Specifically, to measure the coefficient of transmission or transmittance of the outer tube (1), the optical or measurement module (31, 32, 6, 7) comprises a device for measuring the transmittance (32, 7) which has a light emitting source for the transmittance measurement (32), configured to emit a first radiation (T). The light emitting source (32) is oriented so that the outer tube (1) is traversed by the first radiation (T) without intercepting the inner tube (2) thereby producing a first transmitted radiation (T'). The transmittance measurement device further comprises a light detector for measuring the transmittance (7) configured to receive the first transmitted radiation (T'). The resulting measurement is calculated from the signals recorded by the end signal and reference detectors, i.e. from the first radiation (T) and the first transmitted radiation (T').

In a preferred embodiment, the transmittance measurement device (32, 7) comprises:

a light emitting source for measuring the light transmittance, emitting infrared radiation (32IR);

a light detector for measuring the transmittance of infrared radiation (7IR); to cover an infrared spectrum;

a light emitting source for measuring the transmittance, emitting visible and ultraviolet radiation (32UV);

a light detector for measuring the transmittance of visible and ultraviolet radiation (7UV);

to cover a visible and ultraviolet spectrum.

Preferably, the transmittance measurement module (32, 7) is disposed within the spectrophotometer such that during measurement:

the light emitting source for measuring the transmittance (32) is aligned with a chord (C) of the receiver (1,2) and is focused on a first end (C1) of the chord (C), the first end (C1) being located on the outer tube (1); and the light detector for measuring the transmittance (7) is aligned with the chord (C) and focused on a second end (C2) of the chord (C), the second end (C2) being located on the outer tube (1) and opposite the first end (C1).

Chord refers to its common meaning in geometry: line segment between two points of an arc. The chord (C) is defined between the first end (C1) and the second end (C2). The arc is defined by the portion of outer tube (1) comprised between the first end (C1) and the second end (C2).

In the case of the reflectance, the corresponding optical system emits light beams which pass through the outer borosilicate tube (1) twice and are reflected in the inner absorber tube (2). Specifically, to measure the reflection or reflectance coefficient of the inner tube (2), the optical or measurement module (31, 32, 6, 7) comprises a device for measuring the reflectance (31, 6) which has a light emitting source for measurement of the reflectance (31) configured to emit a second radiation (R) emitted to the inner tube (2). The light emitting source (31) is oriented so that the inner tube (2) is intercepted by the second radiation (R) thereby producing a reflected radiation (R'). The reflectance measurement device further comprises a light detector for measuring the reflectance (6) configured to receive the reflected radiation (R') in the inner tube (2). The resulting measurement is calculated from the signals recorded by the end signal and reference detectors, i.e. from the second radiation (R) and the reflected radiation (R') in the inner tube (2). Also, in this calculation, the transmittance measurement of the outer tube previously obtained is deducted.

In a preferred embodiment, the reflectance measurement device (31, 6) comprises:
- a light emitting source for measuring reflectance, emitting infrared radiation (31IR);
- a light detector for measuring the reflectance of infrared radiation (6IR); to cover an infrared spectrum; and
- a light emitting source for measuring the reflectance emitting visible and ultraviolet radiation (31UV);
- a light detector for measuring the reflectance of visible and ultraviolet radiation (6UV);
- to cover a visible and ultraviolet spectrum.

Preferably, the reflectance measurement module (31, 6) is disposed within the spectrophotometer such that during measurement:
- the light emitting source for measuring the reflectance (31) is contained in a longitudinal plane (PL) of the receiver (1,2) and focused on a generatrix (G1) on the outer tube (1);
- the light detector for measuring the reflectance (6) is contained in the longitudinal plane (PL) and focused on the generatrix (G1) on the outer tube (1).

Longitudinal plane (PL) refers to the plane containing the longitudinal axis of the receiver (1, 2) and generatrix (G1) refers to the line parallel to the longitudinal axis on the surface of the outer tube (1).

Preferably, the light emitting source for measuring the reflectance (31) and the light emitting source for measuring the transmittance (32) are in the same sector (S) of the receiver (1, 2). Sector refers to its common meaning in geometry: circular sector: portion of a circle comprised between an arc and the two radii passing through its ends. Thus, the invention refers to a cylindrical sector (S): portion of the cylinder determined by a circular sector projected along the longitudinal axis of the receiver (1, 2). In one embodiment of the invention, the sector (S) is a quadrant, i.e. a 90° sector. The quadrants of the receiver (1, 2) can be seen in the figures showing a cross-section of the receiver (1, 2).

This arrangement of the light emitting source for measuring the reflectance (31) and the light emitting source for measuring the transmittance (32) in the same sector (S) or quadrant allows for a more compact spectrophotometer.

The receiver tubes (1, 2) have a geometry whereby the diameters of both tubes are defined and both are concentric with each other. However the conditions to which they are subjected in solar thermal power plants are such that this concentricity may be altered. The optical channels of the equipment are adapted to the tube geometry, so in order to ensure that the light beams of these channels stream along the optimal path, it is necessary to verify the correct geometry of the tube at the selected measurement point. For this purpose, the equipment has an alignment or concentricity detection system which detects possible movements of the inner tube (2) with respect to its coaxial position with the outer tube (1). This optical alignment system can be formed by an emission LED (8) and an array of photodetectors (or series of photodetectors in a line) (preferably 8 detectors) making it possible to know in real time the relative position between the outer borosilicate tube (1) and the inner steel tube (2). The emission LED can generate a light beam in a cone shape which passes through the tube and is captured by the array of photodetectors situated on the opposite part as shown in FIG. 3. These two elements face each other having an arrangement such that the axis of the cone formed by the emitted light beam is tangent to the inner steel tube (2), when the latter is in its optimum position. With this configuration, the light beam impinges on a portion of the array (9) of photodetectors, while the rest of the array (9) will not detect the beam as it is partly blocked by the inner tube (2). Specifically, to detect concentricity, the concentricity detection module has a light emitting source configured to emit a third radiation (CO) and oriented such that the outer tube (1) is traversed by the third radiation (CO) without intercepting the inner tube (2) producing a second transmitted radiation (CO') which is in turn is received by the array of detectors (9). Therefore, with this optimum configuration as reference, variations of the position of the inner tube (2) can be easily detected, since these will vary the blocking by the tube of the beam emitted and therefore the detection of the array (9) of photodetectors will vary. In those measurement points on the surface of the glass tube and along the length thereof where at least two array detectors are active in having detected the signal, measurements may be taken with an acceptable reliability. In the event that any detector detects a signal due, for instance, to a buckling of the receiver tube (no concentricity between them), the device can either rotate around itself or move on the tube to find an appropriate measurement point thanks to its mechanical conditions.

The mechanical section may comprise several components, the most important being the outer casing (11) which gives the equipment strength and an ergonomic shape with comfortable and intuitive grips that facilitate user manipulation. This outer casing may comprise two half-shells. The lower half-shell (12) with a semi-circular shape to adapt to the outer tube (1), on which all optical and electronic components are fixed except for the screen and keyboard and the upper half-shell (13) which fits over the former thus protecting the electronic and optical systems.

The mechanical section may also have a retractable clamp (10) which is key in adapting the equipment to the receiver tube, also allowing to attach the device to the outer tube (1) in any position. In a preferred embodiment, this mechanical system can consist of three axes (104) longitudinal to the tube which are fixed to the structure of the equipment, plus a fourth axis (105) longitudinal to the tube which is fastened on the hinge clamp. The support of the equipment on the tube is implemented for each axis on 2 rollers (14), which allows a comfortable and simple displacement of the equipment on the outer tube (1) in order to find the correct measurement position. The hinge clamp can be housed inside the equipment when not measuring tubes to facilitate its transfer and storage.

The support rollers (14) and the hinge clamp make it possible to move the device over the glass tube (1) or to rotate the device around itself seeking a suitable position for measurement.

The electronics of the equipment can undertake the data acquisition and processing for both the transmittance module and for the reflectance module. To achieve that the measurement is taken without the influence of ambient light, the data acquisition and processing system may comprise a signal from the emitters which is modulated by sinusoidally varying the supply current of the LEDs (each at a different frequency). This modulation allows to extract the signal of interest in the detectors, filtering out all frequency components except that corresponding to the LED to be used in each case. This filtering is performed by programming a synchronous detection algorithm (lock-in amplification) in a digital signal processor (DSP). That same card generates the modulation signals of the LEDs, enabling the filtering. It is also responsible for the digital acquisition and conversion of the analogical electrical signals measured coming from the photodetectors, as well as for the control via digital outputs of supplying the emission and detection plates.

Furthermore, the photodetectors may be followed by two amplification stages whose gain depends on the value of the resistors they include. One of these resistors may be a digital potentiometer whose value can be controlled via software, allowing to adjust the gain of each channel at any time using the DSP outputs.

For a high-sensitivity measurement, to accurately resolve very small reflectance and transmittance coefficient values or those which are very close to the unit, the acquisition system needs to provide a sufficiently large signal-to-noise ratio. Since the optical background signal comes mainly from ambient sunlight, i.e., it is a signal of great intensity, it may be advisable to apply some kind of processing to said signal to achieve a high signal/noise ratio. The ideal solution in this case is the digital signal processing by applying an extraction algorithm such as synchronous detection or lock-in amplification. To perform such processing, the signal to be measured needs to be easily distinguished from background noise, which is usually achieved by applying some type of modulation to it. This allows field measurements in ambient light, without special darkness or protection conditions.

Another characteristic that gives the equipment great flexibility and makes it easily manipulated and ergonomic, is its user-machine interface. This interface consists of a keyboard or keypad and a screen with which the user can fully communicate with the equipment, and to view the real-time measurements. This interface can incorporate a LED light that allows its use in low or no light atmospheres, such as at night. With such interface, different operating modes and functions of the equipment can be selected.

Figure 6:
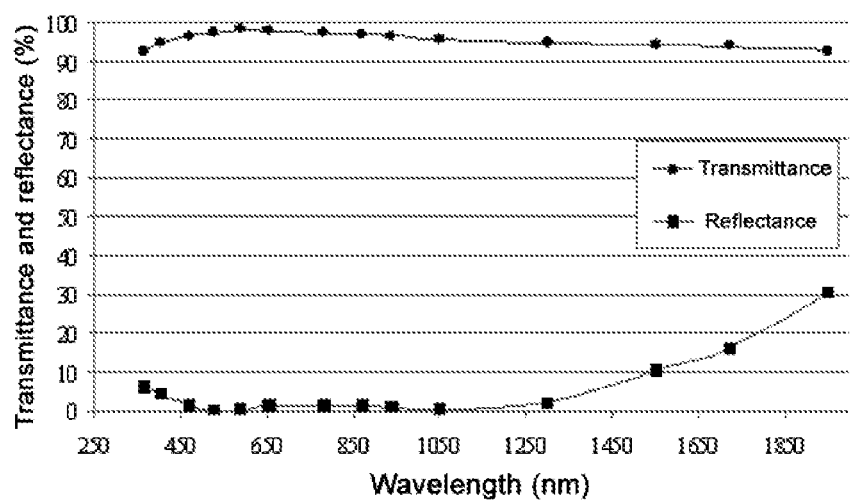
FIG. 6 Graph of reflectivity and transmissivity results according to the wavelength 1 Outer tube, glass tube
2 Inner Tube, absorber tube
3 Integrating sphere
31 Light emitting source, integrating sphere for reflectance measurement
31UV Light emitting source, integrating sphere for reflectance measurement for ultraviolet and visible spectrum
31IR Light emitting source, integrating sphere for reflectance measurement for infrared spectrum
32 Light emitting source, integrating sphere for transmittance measurement
32UV Light emitting source, integrating sphere for transmittance measurement for ultraviolet and visible spectrum
32IR Light emitting source, integrating sphere for transmittance measurement for infrared spectrum
4 Integrating sphere LEDs
6 Light detector for reflectance measurement
6UV Light detector for reflectance measurement for ultraviolet and visible spectrum
6IR Light detector for reflectance measurement for infrared spectrum
7 Light detector for transmittance measurement
7UV Light detector for transmittance measurement for ultraviolet and visible spectrum
7IR Light detector for transmittance measurement for infrared spectrum
8 Light emitting source, auxiliary LED
9 Array of light detectors indicative of concentricity.
10 Clamp
11 Outer casing
12 Lower half-shell
13 Upper half-shell
14 Positioning means, rollers
104 Three axes
105 Fourth axis

The main application of this portable measuring equipment is the on-site evaluation of the optical characteristics of receiver tubes in parabolic trough collectors of solar thermal power plants. These plants have a large number of tubes across large areas of land. So the equipment can incorporate a GPS geo-location system, in order to record the exact geographical location where each measurement is taken. This makes it possible to reconstruct a posteriori the route followed in the evaluation of the solar field as well as specific tubes on which the measurements have been carried out. These results, as well as the status of the equipment can be stored in an external memory unit, which makes it possible to export results quickly and easily to a PC. A specific example of measurement includes the data processing results showing the transmittance and reflectance values of a receiver tube depending on the wavelength, corresponding to a receiver tube of a parabolic trough collector as shown in FIG. 6.

Although the main application of this invention is the use of equipment for on-site evaluation of the optical characteristics of absorber tubes in parabolic trough collectors of solar thermal power plants, its use in other industrial fields requiring measuring equipment with similar characteristics should not be ruled out.

The invention claimed is:

1. A spectrophotometer for the characterization of receivers of solar collectors, each of the receivers having an inner tube and an outer tube, the spectrophotometer comprising:

a measurement module adapted to measure a reflection coefficient and a transmission coefficient of the receiver, the measurement module comprising:

a transmittance measurement device configured to measure a transmission coefficient of the outer tube, the transmittance measurement device comprising:

a first light emitting source adapted to measuring a transmittance, said light emitting source configured to transmit a first radiation, the first radiation being infrared, the light emitting source being oriented such that the outer tube is traversed by the first radiation without intercepting the inner tube so as to produce a first transmitted radiation;

a first light detector adapted to measure the transmission of the first radiation over an infrared spectrum;

a second light emitting source that transmits visible and ultraviolet radiation; and a second light detector that measures the transmission of the visible and ultraviolet radiation over a visible and ultraviolet spectrum, the first and second light emitting sources being aligned with a chord of the receiver and focused on a first end of the chord, the first end being located on the outer tube, the first and second light detectors being aligned with the chord focused on a second end of the chord, the second end being located on the outer tube and opposite the first end;

a reflectance measurement device adapted to measure the reflection coefficient of the inner tube, said reflectance measurement device comprising:

a first light emitting source that measures reflectance, said emitting source emitting a second radiation to the inner tube and oriented such that the inner tube is intercepted by the second radiation so as to produce a reflected radiation, the second radiation being infrared radiation;

a first light detector that measures the reflectance of the infrared radiation over an infrared spectrum;

a second light emitting source that emits visible and ultraviolet radiation; and a second light detector that measure the reflectance of visible and ultraviolet radiation over a visible and ultraviolet spectrum, the first and second light emitting sources being contained in a longitudinal plane of the receiver and focused on a generatrix in the outer tube, the first and second light detectors being contained in the longitudinal plane and focused on the generatrix in the outer tube;

a concentricity detection module adapted to detect a concentricity or a non-concentricity between the inner tube and the outer tube, the concentricity detection module comprising:

an emitting source having a light emitter that detects the concentricity or non-concentricity and configured to emit a third radiation so that the outer tube is traversed by the third radiation without intercepting the inner tube so as to produce a second transmitted radiation; and an array of detectors configured to receive the second transmitted radiation.

2. The spectrophotometer of claim 1, further comprising:
a positioning device with the spectrophotometer so as to rotate the spectrophotometer around a longitudinal axis of the outer tube.

3. The spectrophotometer of claim 1, further comprising:
a processor that measures a calculated coefficient of the outer tube from the first radiation and the first transmitted radiation.

4. The spectrophotometer of claim 1, further comprising:
a processor that measures a reflection coefficient of the inner tube from the second radiation and the reflected radiation in the inner tube.

5. The spectrophotometer of claim 1, wherein the light emitting source for measuring the reflectance and the transmittance are in the same sector of the receiver.

6. The spectrophotometer of claim 1, wherein the emitting source comprising an integrating sphere.

7. The spectrophotometer of claim 1, wherein the emitting source comprises an LED.

8. The spectrophotometer of claim 7, wherein the emitting source comprises a plurality of LEDs.

9. The spectrophotometer of claim 1, further comprising:
a digital circuit that performs analogue/digital acquisition and conversion functions.

10. The spectrophotometer of claim 1, further comprising:
a digital processing card adapted to extract the signal from optical or electrical ambient background noise.

11. The spectrophotometer of claim 1, further comprising:
a screen and a keyboard interfaced with the measurement module.

12. The spectrophotometer of claim 1, further comprising:
a GPS geo-location system cooperative with said measure module.

13. The spectrophotometer of claim 1, further comprising:
an external memory unit cooperative with said measurement module so as to store equipment information and measured values.

14. The spectrophotometer of claim 1, further comprising:
a central control and processing unit cooperative with said measurement module so as to control the measurement module.

15. The spectrophotometer of claim 1, further comprising:
a casing containing said measurement module.

* * * * *